United States Patent
Brand

(12)
(10) Patent No.: US 6,410,771 B1
(45) Date of Patent: Jun. 25, 2002

(54) FLUORINATED COPPER SALTS AS CATALYSTS FOR THE SYNTHESIS OF TRIALKOXYSILANES

(75) Inventor: Alexandra Brand, Darmstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/901,893

(22) Filed: Jul. 11, 2001

(30) Foreign Application Priority Data

Jul. 13, 2000 (DE) ......................................... 100 33 964

(51) Int. Cl.$^7$ .................................................. C07F 7/18
(52) U.S. Cl. ....................................................... 556/470
(58) Field of Search ......................................... 556/470

(56) References Cited

U.S. PATENT DOCUMENTS 5,783,720 A * 7/1998 Mendicino et al. ......... 556/470

FOREIGN PATENT DOCUMENTS

| DE | 199 62 571 | 6/2001 |
|----|------------|--------|
| EP | 0 285 133 | 10/1988 |
| EP | 0 517 398 | 12/1992 |
| JP | 05170773 | 7/1993 |
| JP | 06065257 | 3/1994 |
| JP | 10168084 | 6/1998 |

OTHER PUBLICATIONS

Okamoto et al. "Synthesis of methoxysilanes by the reaction of metallic silicon with methanol using copper (II) acetate as the catalyst" Catalysis Letters vol. 33 (1995) 421–427.

* cited by examiner

*Primary Examiner*—Paul F. Shaver
(74) *Attorney, Agent, or Firm*—Keil & Weinkauf

(57) ABSTRACT

In a process for preparing trialkoxysilanes by reaction of silicon metal with an alcohol in an inert solvent in the presence of a copper catalyst, the copper catalyst used is a copper salt whose anion contains at least one nonhydrolyzable fluorine atom, or a mixture thereof with other salts.

12 Claims, No Drawings

FLUORINATED COPPER SALTS AS CATALYSTS FOR THE SYNTHESIS OF TRIALKOXYSILANES

The present invention relates to a process for preparing trialkoxysilanes by reaction of silicon metal with an alcohol over fluorinated copper salts as catalysts, and to the use of fluorinated copper salts as catalysts in a process for preparing trialkoxysilanes.

Trialkoxysilanes, made up of a silicon atom to which three alkoxy groups and one hydrogen atoms are bound, are very reactive and unstable. They therefore undergo numerous reactions such as additions, copolymerizations, copolycondensations and disproportionation reactions with other organic compounds, giving a series of very useful substances. These are in turn employed as starting materials for silane coupling reagents, coating compositions, heat-resistant surface coatings or for obtaining high-purity monosilanes for semiconductor applications.

Trialkoxysilanes can be prepared by direct reaction of silicon metal with the corresponding alcohols at from 150 to 500° C. in the presence of copper-containing catalysts (direct synthesis). Here, the copper-containing silicon contact composition is generally suspended in an inert, liquid reaction medium and converted into the desired trialkoxysilanes at from 150 to 300° C. by introducing liquid or gaseous alcohol. In terms of the conversion of silicon metal and the selectivity to the trialkoxysilane relative to the tetraalkoxysilane formed as by-product, copper(I) chloride has been found to be a particularly suitable catalyst.

M. Okamoto et al., Catalysis Lett. 1995, 33, 421 to 427, reports a study of the reaction of silicon metal with methanol over various copper catalysts in a reactor containing a fixed silicon bed. The copper catalysts copper(I) oxide, copper(II) oxide, copper(II) acetate, copper(II) formate, copper(II) phthalate, copper(II) oxalate and copper(I) chloride were compared. Copper(I) chloride gave the highest silicon conversions (88%) and selectivities to trimethoxysilane relative to tetramethoxysilane (98%).

However, the use of copper(I) chloride results in formation of hydrochloric acid which makes it necessary to use expensive, corrosion-resistant materials for the reactors employed. Furthermore, the presence of chloride in the reaction mixture and the product leads to a reduction in the yield of trialkoxysilane, since the subsequent reaction of trialkoxysilane with alcohols to give tetraalkoxysilane is catalyzed by chloride. The hydrochloric acid formed when using copper(I) chloride as catalyst can, when methanol is used as alcohol, react with the methanol to form methyl chloride and water, so that methanol is lost as starting material for the trialkoxysilane synthesis.

For these reasons, the use of catalysts which do not contain any hydrolyzable halide is desirable.

JP-A-05170773 describes the preparation of trialkoxysilanes by reaction of silicon metal with alcohol in the presence of copper alkoxides. This reaction gives halide-free products. The selectivity of the reaction is from 91 to 92%, but the conversion of silicon is only from 21 to 32.4%.

An increase in the selectivity and the silicon conversion of this reaction is achieved according to JP-A-06065257 by use of a copper alkoxide catalyst in combination with a metal halide. However, the presence of halide in the reaction mixture and in the reaction product has the abovementioned disadvantages.

EP-A-0285133 relates to the preparation of trialkoxysilanes by reaction of silicon metal with alcohols using a copper(II) hydroxide catalyst. In this reaction, silicon conversions of from about 80 to 90 mol % are achieved and the proportion of tetraalkoxysilanes in the reaction mixture is from about 5 to 10 mol %, based on the silicon.

JP-A-10168084 relates to the preparation of trialkoxysilanes by reaction with silicon metal and alcohol over a copper(II) oxide catalyst having a water content of <3000 ppm. In the preparation of triethoxysilane, a selectivity coefficient for trialkoxysilane of 85.2 mol % and a silicon conversion of 91% by weight are achieved. However, the low water content of the catalyst used can require thermal pretreatment of the catalyst and thus an additional reaction step.

EP-A 0 517 398 discloses a process for preparing alkoxysilanes of the formula $(OR)_n SiH_{4-n}$, where n=2, 3 or 4, by reacting silicon with a solution of hydrogen fluoride or a salt which can be hydrolyzed to form hydrogen fluoride in a liquid primary or secondary alcohol, with or without addition of a copper catalyst. However, the use of hydrogen fluoride is problematical, since hydrogen fluoride is extremely toxic and attacks glass. Furthermore, the actual reaction has to be preceded by a pretreatment step in this process, since $CuF_2$ itself is inactive as catalyst.

It is an object of the present invention to provide a copper catalyst for the synthesis of trialkoxysilanes, which makes it possible to achieve a high selectivity to trialkoxysilane relative to tetraalkoxysilane and high conversions without the presence of hydrolyzable halide being necessary. No time-consuming preactivation for generation of a catalytically active species should be required.

The achievement of this object starts out from a process for preparing trialkoxysilanes by reaction of silicon metal with an alcohol in an inert solvent in the presence of a copper catalyst.

In the process of the present invention, the copper catalyst used is a copper salt whose anion contains at least one nonhydrolyzable fluorine atom, or a mixture thereof with other salts.

Preferred anions containing nonhydrolyzable fluorine atoms are selected from among fluoro complexes of carbon, sulfur, phosphorus and boron. Particular preference is given to trifluoroacetate, trifluorosulfonate, hexafluorophosphate and tetrafluoroborate. Very particular preference is given to trifluoroacetate, trifluorosulfonate and tetrafluoroborate.

Preference is given to using the copper(II) salts of the anions containing nonhydrolyzable fluorine atoms.

The problem of corrosion of the apparatuses used is significantly reduced compared to the use of copper chlorides as catalysts. Since the copper salts used contain only nonhydrolyzable fluoride, glass apparatuses can be used without the risk of the glass being attacked.

The reaction product of the reaction according to the present invention, namely trialkoxysilane is significantly stabilized against further reaction to form tetraalkoxysilane, in contrast to reaction products produced using copper chlorides.

The copper salts of anions containing nonhydrolyzable fluorine atoms which are used according to the present invention are commercially available. They can be obtained, for example, by reacting copper salts such as $Cu(OH)_2$ with the appropriate acids, e.g. trifluoroacetic acid, trifluorosulfonic acid, hexafluorophosphoric acid, tetrafluorophosphoric acid or tetrafluoroboric acid.

High silicon conversions and very good selectivities to trialkoxysilane relative to tetraalkoxysilane are achieved by means of the process of the present invention. In general, silicon conversions at the end of the reaction of >75 mol % are achieved, preferably from 80 to 90 mol %, particularly preferably from 82 to 90 mol %. Here, the silicon conversion is determined according to the following equation: Si[mol] in the product/amount of silicon used*100.

The selectivity to trialkoxysilane relative to tetraalkoxysilane is generally greater than 80 mol %, preferably from 85 to 95 mol %. Here, the selectivity is determined according to the following equation: trialkoxysilane[mol]/trialkoxysilane[mol]+tetraalkoxysilane[mol])* 100. Activation of the catalyst used according to the present invention by reduction or by means of a thermal treatment at high temperatures is not necessary.

In a further embodiment of the process of the present invention, further salts are used in addition to the copper salts whose anions contain nonhydrolyzable fluorine atoms which are used according to the present invention. These additional salts can be salts which are themselves catalytically active or can be additives for improving the reaction parameters.

The amount of further salts present is usually from 0 to 20% by weight, preferably from 0.5 to 5% by weight, based on the copper salt whose anion contains nonhydrolyzable fluorine atoms.

Suitable salts which are themselves catalytically active are selected from among $Cu_2O$, $CuO$, $Cu(OH)_2$, $CuCl$, $CuCl_2$, $Cu(ac)_2$ and $CuSO_4$; preferred salts are $Cu_2O$, $CuO$ and $Cu(OH)_2$.

Apart from high silicon conversions and a very good selectivity to trialkoxysilane, relative to tetraalkoxysilane, the process of the present invention displays very good product formation rates for trialkoxysilanes.

The amount of copper salt whose anion contains nonhydrolyzable fluorine atoms used in the process of the present invention can be varied within a wide range. Use is generally made of from 0.0001 to 0.05 mol, preferably from 0.0005 to 0.005 mol, particularly preferably from 0.001 to 0.005 mol, of catalyst per mole of silicon metal.

The alcohol used in the process of the present invention is generally a monohydric alcohol. Preference is given to using an alcohol ROH in which R is an alkyl group having from 1 to 6 carbon atoms. This alkyl group can be branched or unbranched, but is preferably unbranched. The alkyl group of the alcohol used preferably has from 1 to 3 carbon atoms; particular preference is given to using methanol or ethanol and very particular preference is given to using methanol, so that the very particularly preferred product is trimethoxysilane. The alcohol is usually introduced in liquid or gaseous form into a reaction mixture comprising reaction medium, silicon metal and catalyst.

The alcohol is generally added continuously in excess to the initially charged silicon metal (semibatch process). The precise ratio of alcohol to silicon metal depends, inter alia, on the desired work-up method, since an excessively high MeOH content in the product sometimes has to avoided.

As silicon metal, it is in principle possible to use any commercially available product. A typical composition of a commercial product suitable for the process of the present invention comprises from about >98 to 99% by weight of Si, <1% by weight of Fe, from about 0.05 to 0.7% by weight of Al, from about 0.001 to 0.1% by weight of Ca, <0.001% by weight of Pb and <0.1% by weight of water. Customary particle diameters are from 45 to 600 μm, preferably from 75 to 300 μm. In general, small particle diameters of the silicon metal are preferred, since they are easier to disperse and react more quickly.

Inert solvents which are suitable for the process of the present invention are thermally stable solvents which do not decompose at the high temperatures necessary for the process of the present invention. Preferred solvents are high-temperature-stable organic solvents which are usually employed as heat transfer media. The type of solvent used has a considerable influence on the reaction of silicon metal with alcohol over copper catalysts. Particularly suitable solvents are Therminal® 59, Therminol® 60, Therminol® 66, Dowtherm® HT, Marlotherm® S, Marlotherm® L, diphenyl ether, biphenyl, terphenyl and alkylated benzenes, alkylated biphenyls and alkylated terphenyls and also reaction media comprising diphenylalkanes as are disclosed in the German patent application number 19962571.9, which is not a prior publication. The solvents mentioned have boiling points at atmospheric pressure which are higher than about 250° C. Therminol® 59 is a product of the Monsanto Company which (according to the safety data sheet) is a mixture of diphenylethane, ethyldiphenylethane, diethyldiphenylethane and ethylbenzene. Therminol® 60 is a mixture of polyaromatic compounds having a mean molecular weight of 250. The optimum use temperature of Therminol® 60 is in the range from −45 to 315° C. Therminol® 66 and Dowtherm® HT are mixtures of hydrogenated terphenyls having a mean molecular weight of 240. Their upper temperature limit is about 370° C. Marlotherm® S, a product of Hüls AG, is a mixture of isomeric dibenzylbenzenes and Marlotherm® L, likewise a product of Hüls AG, is a mixture of isomeric benzyltoluenes. Particularly suitable solvents are Therminol® 59, Therminol® 66, Marlotherm® S, Marlotherm® L and also alkylated benzenes, tritoluenes and tetratoluenes and reaction media comprising diphenylalkanes.

The alkyl chains of the diphenylalkanes generally have a chain length of from 3 to 20 carbon atoms, preferably from 10 to 14 carbon atoms. The alkyl chains can be linear or branched. Preference is given to using diphenylalkanes having linear alkyl chains. For price reasons, particular preference is given to using a mixture of diphenylalkanes having alkyl chains of from 10 to 14 carbon atoms as reaction medium.

The amount of solvent used can be varied. Normally, for cost reasons, a silicon:solvent ratio of from 2:1 to 1:4, preferably from 2:1 to 1:2, is sought.

A residual content of organic chlorine compounds in the reaction medium does not have a significant adverse effect on the reaction. Residual contents of generally from 0 to 10 000 ppm, preferably from 1 to 1000 ppm, particularly preferably from 100 to 500 ppm, based on the reaction medium, can be present in the reaction medium. These organic chlorine compounds do not result in increased corrosivity of the reaction medium.

The water content of the reaction medium has no influence on the reaction provided that it is relatively low. Usual water contents are from 0 to 1000 ppm, preferably from 1 to 100 ppm, particularly preferably from 10 to 50 ppm, based on the reaction medium. However, larger amounts of water which can, for example, be introduced with the alcohol have an adverse effect.

The reaction is generally carried out at from 150 to 300° C., preferably from 180 to 300° C. In some cases, increasing the temperature while maintaining otherwise constant reaction conditions leads to an increase in the selectivity, i.e. to an improvement in the ratio of trialkoxysilane to the tetraalkoxysilane formed as an undesirable by-product. The reaction pressure is not critical. The reaction is usually carried out at atmospheric pressure.

In one embodiment of the process of the present invention, the inert solvent, the silicon metal and the copper salt used as catalyst according to the present invention, if desired in admixture with further salts, are placed in a reactor. The mixture is generally heated to the desired reaction temperature and the alcohol is introduced as a liquid or gas into the mixture. After the reaction is complete, the reaction medium can be recovered by filtration and reused. During the reaction, further silicon metal can be added at particular time intervals. Further catalyst can be introduced at the same time. If no further catalyst is added, a slight, noncritical decrease in the reactivity of the mixture may be found. In this way, at least ten times, preferably from ten to fifty times, the amount of silicon metal initially introduced into the reaction medium used can be reacted.

In the table:
Ex. Example, number of the experiment
Temp.: Reaction temperature in °C.
MeOH throughput: Throughput of methanol in g per minute and per kg of silicon
Catalyst: Catalyst used and amount of catalyst used in g per kg of silicon
Si conversion: Molar amount of silicon in the product per molar amount of silicon used, in percent
Selectivity: Selectivity to trimethoxysilane relative to tetramethoxysilane: trimethoxysilane[mol]/(trimethyoxysilane[mol]+tetramethoxysilane[mol])*100

TABLE 1

| Ex. No. | Temp. (°C.) | Solvent | MeOH through-put (g/min kg$_S$) | Catalyst Type | (g/kg$_{Si}$) | Balance time (h) | Si conversion (%) | Selectivity TMS/ (TMS + TTMS) [1] [mol] (%) | Methanol conversion (%) | Reaction time (TMS < 1%) (h) |
|---|---|---|---|---|---|---|---|---|---|---|
| 1 | 250 | Marlo-therm ® S | 3.10 | Cu(O$_3$SCF$_3$)$_2$ | 20.70 | 22.5 | 79.3 | 90.37 | 66.14 | 25.0 |
| 2 | 250 | Marlo-therm ® S | 3.09 | Cu(OOCCF$_3$)$_2$ | 10.40 | 22.5 | 78.4 | 90.92 | 66.38 | 25.5 |
| 3 | 250 | Marlo-therm ® S | 3.12 | Cu(BF$_4$)$_2$ | 16.00 | 22.5 | 80.3 | 89.48 | 67.52 | 24.0 |
| Comp. ex. | 250 | Marlo-therm ® S | 3.10 | Cu(OH)$_2$ | 6.60 | 22.5 | 81.2 | 92.20 | 67.69 | 25.0 |

| Ex. No. | Si conversion (%) | Selectivity TMS (TMS + TTMS) [mol] (%) | Methanol conversion (%) | Si rate [%/h] | Conversion rate of TMS [g/h] |
|---|---|---|---|---|---|
| 1 | 79.4 | 90.19 | 60.05 | 3.18 | 24.92 |
| 2 | 81.4 | 87.04 | 60.95 | 3.19 | 24.18 |
| 3 | 83.5 | 88.92 | 60.96 | 3.40 | 26.92 |
| Comp. ex. | 83.7 | 90.11 | 62.99 | 3.35 | 26.25 |

[1] TMS: trimethoxysilane   TTMS: tetramethoxysilane

The present invention further provides for the use of copper salts whose anions contain at least one nonhydrolyzable fluorine atom, or mixtures thereof with other salts, as catalysts for preparing trialkoxysilanes by reaction of silicon metal with an alcohol.

The following examples illustrate the invention.

EXAMPLES

Preparation of Trimethoxysilane

General method for all examples below:

500 ml of solvent, 200 g of metallic silicon (average particle diameter: 200 μm, silicon content: >98%) and about 0.02–0.01% by weight, based on the silicon metal, of the copper salt whose anion contains nonhydrolyzable fluorine atoms are placed in a 500 ml glass reactor.

The reactor is equipped with a thermometer, condenser, stirrer and inlet tube for the alcohol and for nitrogen. The reaction mixture is heated to the reaction temperature indicated in Table 1, and liquid methanol is metered in. Shortly after the commencement of methanol addition, product begins to condense in the condenser. The composition of the product is determined by means of gas chromatography.

To enable the results to be compared, a balance was carried out to a uniform reaction time of 22.5 h. In addition, the balance to the end of the reaction was also examined (after 24 and 25.5 h, methanol content of the product= 100%). The reaction mixture at the end of the reaction is a reddish brown suspension which is filtered. The recovered solvent can be reused.

Table 1 shows the reaction parameters and experimental results for the examples according to the present invention and the comparative example.

We claim:

1. A process for preparing trialkoxysilanes by reaction of silicon metal with an alcohol in an inert solvent in the presence of a copper catalyst, wherein the copper catalyst used is a copper salt whose anion contains at least one nonhydrolyzable fluorine atom, or a mixture thereof with other salts.

2. A process as claimed in claim 1, wherein the anion of the copper salt containing at least the nonhydrolyzable fluorine atom is selected from the group of trifluoroacetate, trifluorosulfonate, hexafluorophosphate and tetrafluoroborate.

3. A process as claimed in claim 1, wherein the other salts are selected from the group CU$_2$O, CuO, Cu(OH)$_2$, CuCl, CuCl$_2$, Cu(ac)$_2$ and CuSO$_4$.

4. A process as claimed in claim 1, wherein the anion of the copper salt containing at least the nonhydrolyzable fluorine atom is selected from the group of trifluoroacetate, trifluorosulfonate, hexafluorophosphate and tetrafluoroborate and wherein the other salts are selected from the group Cu$_2$O, CuO, Cu(OH)$_2$, CuCl, CuCl$_2$, Cu(ac)$_2$ and CuSO$_4$.

5. A process as claimed in claim 1, wherein the alcohol is ROH in which R is an alkyl group having from 1 to 6 carbon atoms.

6. A process as claimed in claim 5, wherein ROH is methanol.

7. A process as claimed in claim 1, wherein the inert solvent is selected from the group of Therminol® 66, Marlotherm® S, Marlotherm® L, alkylated benzenes, tritoluenes and tetratoluenes and reaction media comprising diphenylalkanes.

8. A process as claimed in claim 1, wherein the alcohol is ROH in which R is an alkyl group having from 1 to 6 carbon atoms and wherein the inert solvent is selected from the group of Therminol® 66, Marlotherm® S, Marlotherm® L, alkylated benzenes, tritoluenes and tetratoluenes and reaction media comprising diphenylalkanes.

9. A process as claimed in claim 4, wherein the alcohol is ROH in which R is an alkyl group having from 1 to 6 carbon atoms and wherein the inert solvent is selected from the group of Therminol® 66, Marlotherm® S, Marlotherm® L, alkylated benzenes, tritoluenes and tetratoluenes and reaction media comprising diphenylalkanes.

10. A process as claimed in claim 1, wherein the reaction is carried out at from 150 to 300° C.

11. A process as claimed in claim 3, wherein the other salts are selected from the group $Cu^2O$, $CuO$ and $Cu(OH)_2$.

12. A process as claimed in claim 4, wherein the other salts are selected from the group $Cu_2O$, $CuO$ and $Cu(OH)_2$.

* * * * *

UNITED STATES PATENT AND TRADEMARK OFFICE
CERTIFICATE OF CORRECTION

PATENT NO.    : 6,410,771 B1
DATED         : June 25, 2002
INVENTOR(S)   : Brand et al.

It is certified that error appears in the above-identified patent and that said Letters Patent is hereby corrected as shown below:

Column 6,
Line 48, "$CU_2O$" should be -- $Cu_2O$ --.

Column 8,
Line 4, "$Cu^2O$" should be -- $Cu_2O$ --.

Signed and Sealed this

Fifteenth Day of October, 2002

Attest:

Attesting Officer

JAMES E. ROGAN
*Director of the United States Patent and Trademark Office*